United States Patent
Liu (10) Patent No.: US 12,383,154 B2
(45) Date of Patent: Aug. 12, 2025

(54) CAPACITIVE ACCELEROMETER DEVICE AND SENSING METHOD THEREOF

(71) Applicant: Chia-Hsing Liu, Taipei (TW)

(72) Inventor: Chia-Hsing Liu, Taipei (TW)

(73) Assignee: Chia-Hsing Liu (TW)

( * ) Notice: Subject to any disclaimer, the term of this patent is extended or adjusted under 35 U.S.C. 154(b) by 395 days.

(21) Appl. No.: 16/112,878

(22) Filed: Aug. 27, 2018

(65) Prior Publication Data

US 2019/0183365 A1    Jun. 20, 2019

(30) Foreign Application Priority Data

Dec. 15, 2017   (TW) ................ 106144210
May 4, 2018     (TW) ................ 107115245

(51) Int. Cl.
*A61B 5/024* (2006.01)
*A61B 5/00* (2006.01)
(Continued)

(52) U.S. Cl.
CPC ...... *A61B 5/02444* (2013.01); *A61B 5/02007* (2013.01); *A61B 5/02035* (2013.01);
(Continued)

(58) Field of Classification Search
None
See application file for complete search history.

(56) References Cited

U.S. PATENT DOCUMENTS 5,941,837 A * 8/1999 Amano ................ A61B 5/6822
                                                         600/595
2004/0032957 A1* 2/2004 Mansy ................... A61B 7/04
                                                          381/67
(Continued)

FOREIGN PATENT DOCUMENTS

CN     202537490 U    11/2012
CN     103961080 A     8/2014
(Continued)

OTHER PUBLICATIONS

Goverdovsky, Valentin, et al. "Co-located multimodal sensing: A next generation solution for wearable health." IEEE Sensors Journal 15.1 (2014): 138-145. (Year: 2014).*
(Continued)

*Primary Examiner* — Puya Agahi
*Assistant Examiner* — Jairo H Portillo (57) ABSTRACT

A capacitive accelerometer device is provided, and includes a capacitive accelerometer module, a display device and a signal line. The capacitive accelerometer module includes one or more capacitive accelerometers for sensing an arterial acceleration pulse wave of a user. The display device includes a displayer and a speaker. The displayer is used to display the arterial acceleration pulse wave of the user. The speaker emits an audible signal according to a change value of the arterial acceleration pulse wave. The display device electrically connects to the capacitive accelerometer module via the signal line. The display device automatically senses the arterial acceleration pulse wave of the user and correspondingly generates the change value. The display device generates a prompt signal when the change value is equal to or larger than a predetermined value.

9 Claims, 9 Drawing Sheets

(51) Int. Cl.
*A61B 5/02* (2006.01)
*A61B 5/0285* (2006.01)
*A61B 5/11* (2006.01)
*A61B 7/04* (2006.01)

(52) U.S. Cl.
CPC ........ *A61B 5/02438* (2013.01); *A61B 5/0285* (2013.01); *A61B 5/1102* (2013.01); *A61B 5/4866* (2013.01); *A61B 5/6824* (2013.01); *A61B 5/6826* (2013.01); *A61B 5/6831* (2013.01); *A61B 5/6898* (2013.01); *A61B 5/7278* (2013.01); *A61B 5/7282* (2013.01); *A61B 5/7415* (2013.01); *A61B 5/7445* (2013.01); *A61B 7/04* (2013.01); *A61B 2560/0443* (2013.01); *A61B 2562/0219* (2013.01); *A61B 2562/227* (2013.01)

(56) References Cited

U.S. PATENT DOCUMENTS

| | | | | |
|---|---|---|---|---|
| 2006/0135863 | A1* | 6/2006 | Birnbaum | A61B 5/0002 600/388 |
| 2006/0247542 | A1* | 11/2006 | Watanabe | A61B 5/16 600/483 |
| 2007/0118028 | A1* | 5/2007 | Kitajima | A61B 5/6838 600/310 |
| 2008/0081963 | A1* | 4/2008 | Naghavi | A61B 5/6806 600/301 |
| 2008/0192963 | A1* | 8/2008 | Sato | H04R 19/04 381/174 |
| 2014/0111340 | A1 | 4/2014 | Zohar | |
| 2015/0141774 | A1* | 5/2015 | Ogawa | A61B 5/7246 340/870.07 |
| 2016/0199002 | A1* | 7/2016 | Lee | A61B 5/7246 340/870.07 |
| 2016/0310025 | A1* | 10/2016 | Viellard-Boutry | A61B 5/02125 |
| 2016/0324470 | A1* | 11/2016 | Townsend | G06F 1/163 |
| 2018/0008175 | A1* | 1/2018 | Ishizawa | A61B 5/02416 |
| 2020/0117417 | A1* | 4/2020 | Bowler, II | G10L 15/28 |

FOREIGN PATENT DOCUMENTS

| | | | |
|---|---|---|---|
| CN | 104590111 A | 5/2015 | |
| CN | 105813550 A | 7/2016 | |
| JP | 5300886 A | 11/1993 | |
| JP | 20096113 A | 1/2009 | |
| JP | 201423141 A | 2/2014 | |
| JP | 201497242 A | 5/2014 | |
| JP | 20152360 A | 1/2015 | |
| JP | 201525769 A | 2/2015 | |
| WO | WO-2015193551 A1 * | 12/2015 | .......... A61B 5/0022 |
| WO | 2016167202 A1 | 10/2016 | |
| WO | 2016174839 A1 | 11/2016 | |

OTHER PUBLICATIONS

Lee, Youngbum, et al. "Implementation of wearable sensor glove using pulse-wave sensor, conducting fabric and embedded system." 2006 3rd IEEE/EMBS International Summer School on Medical Devices and Biosensors. IEEE, 2006. (Year: 2006).*

Elgendi, Mohamed, et al. "Detection of a and b waves in the acceleration photoplethysmogram." Biomedical engineering online 13.1 (2014): 1-18. (Year: 2014).*

Nomura, Shusaku, Yasushi Hanasaka, and Hiroshi Ogawa. "Multiple pulse wave measurement toward estimating condition of human arteries." IADIS International Journal on WWW/Internet 11.3 (2013). (Year: 2013).*

Yonei, Yoshikazu, et al. "Effects of health food containing Cistanche deserticola extract on QOL and safety in elderly: An open pilot study of 12-week oral treatment." Anti-Aging Medicine 8.2 (2011): 7-14. (Year: 2011).*

Wang Yong-Hua, et al., "Clinical Hearing Aids Science," Anhui science & technology press, Feb. 28, 2005, pp. 8-10.

Wang De-Shan, et al., "Integrated Chinese and Western Physiology," Traditional Chinese Medicine press, Jan. 31, 2010, pp. 263-270.

* cited by examiner

CAPACITIVE ACCELEROMETER DEVICE AND SENSING METHOD THEREOF

CROSS-REFERENCE TO RELATED PATENT APPLICATION

This application claims the benefit of priority to Taiwan Patent Application No. 106144210, filed on Dec. 15, 2017, and Taiwan Patent Application No. 107115245, filed on May 4, 2018. The entire content of the above identified application is incorporated herein by reference.

BACKGROUND OF THE INVENTION

1. Field of the Invention

The present disclosure relates to an accelerometer device, and more particularly to a capacitive accelerometer device and sensing method thereof.

2. Description of Related Art

Due to technological advancement over the years, convenient sensing devices can now partially replace large medical devices, such as sensing heartbeats with smart bracelets. In recent years, multi-functional sensing devices have become more popular, and smart watches can be used to play music and sense heartbeat. However, a general sensing device does not have a function of comparing normal values with abnormal values, which lacks applicability.

SUMMARY OF THE INVENTION

A capacitive accelerometer device is provided according to an embodiment of the present disclosure, and applied to sense an arterial acceleration pulse wave of a user. The capacitive accelerometer device includes a capacitive accelerometer module, a display device and a signal line. The capacitive accelerometer module includes one or more capacitive accelerometers. Each of the capacitive accelerometers is used to sense the arterial acceleration pulse wave of the user. The display device includes a displayer and a speaker. The displayer is used to display the arterial acceleration pulse wave of the user. The speaker emits an audible signal according to a change value of the arterial acceleration pulse wave. The display device is connected to a fixing bracket via a connector. The fixing bracket has a clasp for snapping the display device on a wrist of the user. The display device is applied to a smart bracelet, a smart phone, a desktop computer, a laptop computer, a dedicated monitor or a tablet computer. The display device automatically senses the arterial acceleration pulse wave of the user and correspondingly generates the change value. The display device generates a prompt signal when the change value is equal to or larger than a predetermined value.

A sensing method is provided according to another embodiment of the present disclosure, used in a capacitive accelerometer device, and applied to sense an arterial acceleration pulse wave of a user. The sensing method includes: sensing the arterial acceleration pulse wave of the user in a contact manner by one or more capacitive accelerometers included in a capacitive accelerometer module; displaying the arterial acceleration pulse wave of the user by a displayer included in a display device; and emitting an audible signal according to a change value of the arterial acceleration pulse wave by a speaker included in a display device. The display device connects to a fixing bracket via a connector. The fixing bracket has a clasp for snapping the display device on a wrist of the user. The display device is applied to a smart bracelet, a smart phone, a desktop computer, a laptop computer, a dedicated monitor or a tablet computer. The display device automatically senses the arterial acceleration pulse wave of the user and correspondingly generates the change value. The display device generates a prompt signal when the change value is equal to or larger than a predetermined value.

For further understanding of the instant disclosure, reference is made to the following detailed description illustrating the embodiments of the instant disclosure. The description is only for illustrating the instant disclosure, not for limiting the scope of the claims.

DETAILED DESCRIPTION OF THE PREFERRED EMBODIMENTS

Figure 1:
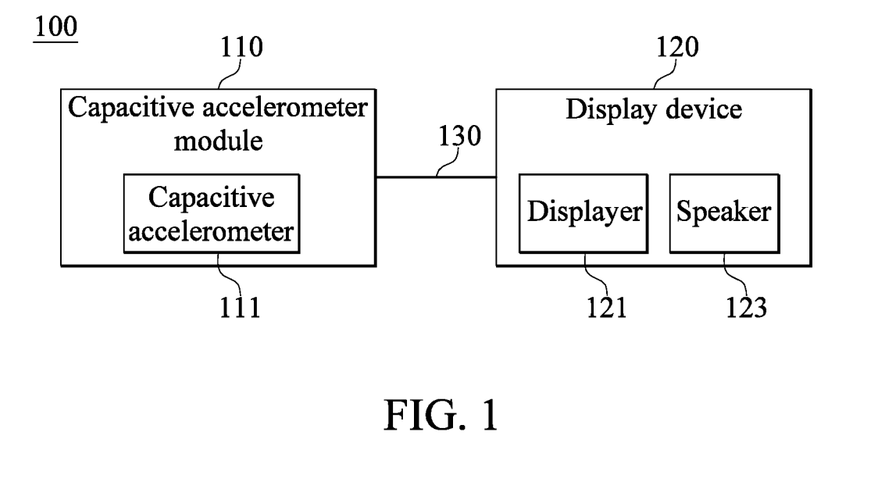
FIG. 1 shows a block diagram of a capacitive accelerometer device depicted in accordance with an exemplary embodiment of the present disclosure.

Reference is made to FIG. 1, which shows a block diagram of a capacitive accelerometer device depicted in accordance with an exemplary embodiment of the present disclosure.

The capacitive accelerometer device 100 includes a capacitive accelerometer module 110 and a display device 120. The capacitive accelerometer device 100 is used to sense an arterial acceleration pulse wave of a radial artery, a brachial artery, a carotid artery, a subclavian artery, a foot artery or a head artery of a user. The present disclosure is not limited to the types of artery disclosed herein. The capacitive accelerometer device 100 is used to sense the user. The capacitive accelerometer module 110 includes one or more capacitive accelerometers 111. Each of the capacitive accelerometers 111 is used to sense the arterial acceleration pulse wave of the user in a contact manner. For example, the capacitive accelerometer module 110 can sense the arterial acceleration pulse wave of the carotid artery of the user. The capacitive accelerometer module 110 can sense the arterial acceleration pulse wave of the radial artery of the user. Furthermore, the capacitive accelerometers 111 can be a condenser microphone. The condenser microphone can be an electret condenser microphone or a micro-electromechanical condenser microphone. The electret condenser microphone or the micro-electromechanical condenser microphone used by the capacitive accelerometer device 100 of the present disclosure are used to increase a sensitivity of sensing the arterial acceleration pulse wave of the user and decrease manufacturing costs. The capacitive accelerometer device 100 can be applied to a mobile device.

The display device 120 includes a displayer 121 and a speaker 123. The displayer 121 is used to display the arterial acceleration pulse wave of the user. The speaker 123 emits an audible signal according to a change value of the arterial acceleration pulse wave. The display device 120 connects to a fixing bracket via a connector (not shown). The fixing bracket has a clasp for snapping the display device 120 on a wrist of the user (not shown). Furthermore, the display device 120 further includes a signal line 130, an analog-to-digital converter (not shown) and a central processor (not shown). The display device 120 electrically connects to the capacitive accelerometer module 110 via the signal line 130. The analog-to-digital converter connects between the capacitive accelerometer module 110 and the central processor. The analog-to-digital converter converts an analog signal of the arterial acceleration pulse wave sensed by the capacitive accelerometers 111 of the capacitive accelerometer module 110 to a digital signal of the arterial acceleration pulse wave and transmits the digital signal to the central processor. The central processor has appropriate hardware, software and firmware with a function of feature extraction for converting the detected arterial acceleration pulse waves before and after a meal, a heart rate, a heart rate variability, a respiration rate, a blood pressure, a fatigue index, etc. Furthermore, the display device further includes a button. When the user presses the button, the displayer 121 correspondingly displays the heart rate, the heart rate variability, the respiration rate, the blood pressure and the fatigue index according to the detected arterial acceleration pulse wave before and after the meal. In addition, the capacitive accelerometer 111 can connect to the capacitive accelerometer module 110 by snap-fastening to increase a flexibility in replacing the capacitive accelerometer. Since the capacitive accelerometer senses the arterial acceleration pulse wave of the user in a contact manner, and the user's skin may have small amounts of bacteria, a replaceable capacitive accelerometer can increase a cleanliness of the capacitive accelerometer device 100.

The display device 120 automatically senses the arterial acceleration pulse wave of the user and correspondingly generates the change value. The display device 120 generates a prompt signal when the change value is equal to or larger than a predetermined value. For example, the display device 120 can include a communication device (not shown). When the change value of the arterial acceleration pulse wave of the user is equal to or larger than the predetermined value, the communication device of the display device 120 transmits the prompt signal to a remote electronic device through the wireless communication mode, which is suitable for the home care of a patient, and informs remote relatives or the medical team that the health condition of the patient may be abnormal. In addition, the capacitive accelerometer device 100 may also sense an arterial acceleration pulse wave of an animal. The display device 120 may be applied to a smart bracelet, a smart phone, a desktop computer, a laptop computer, a dedicated monitor or a tablet computer.

Figure 2:
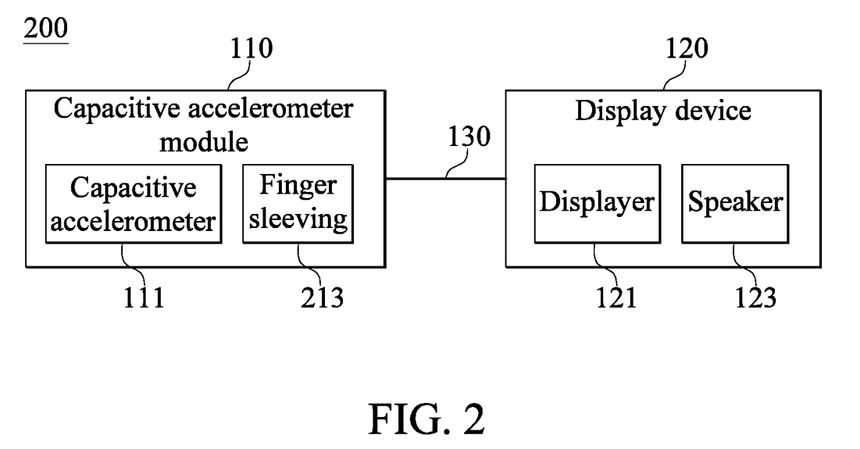
FIG. 2 shows a block diagram of a capacitive accelerometer device depicted in accordance with another exemplary embodiment of the present disclosure.

Reference is made to FIG. 2, which shows a block diagram of a capacitive accelerometer device depicted in accordance with another exemplary embodiment of the present disclosure.

The capacitive accelerometer device 200 includes a capacitive accelerometer module 110, a display device 120 and a signal line 130. Furthermore, the capacitive accelerometer module 110 further includes one or more finger sleevings 213. Each of the finger sleevings 213 is used for being sleeved on a finger of the user.

Figure 3A:
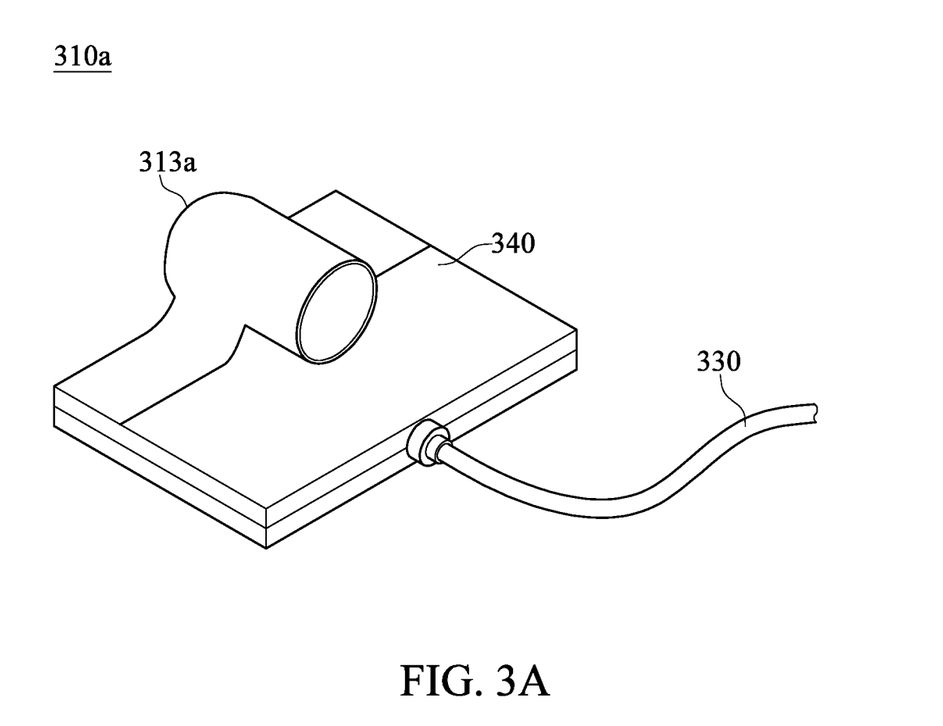
FIG. 3A is a schematic view showing an appearance of a capacitive accelerometer device depicted in accordance with an exemplary embodiment of the present disclosure.

Reference is made to FIG. 3A, which is a schematic view showing an appearance of a capacitive accelerometer device depicted in accordance with an exemplary embodiment of the present disclosure.

The capacitive accelerometer module 310a has a finger sleeving 313a, a signal line 330 and a circuit board 340. The signal line 330 electrically connects to the circuit board 340. The finger sleeving 313a is sleeved on a middle finger of the user. The capacitive accelerometer (not shown) is disposed on a side of the finger sleeving. For example, the capacitive accelerometer can be disposed on the other side of a contact point of the finger sleeving 313a and the circuit board 340 (a back side of the circuit board 340). The capacitive accelerometer senses the arterial acceleration pulse wave of the user through a pulse received by the finger sleeving 313a.

Figure 3B:
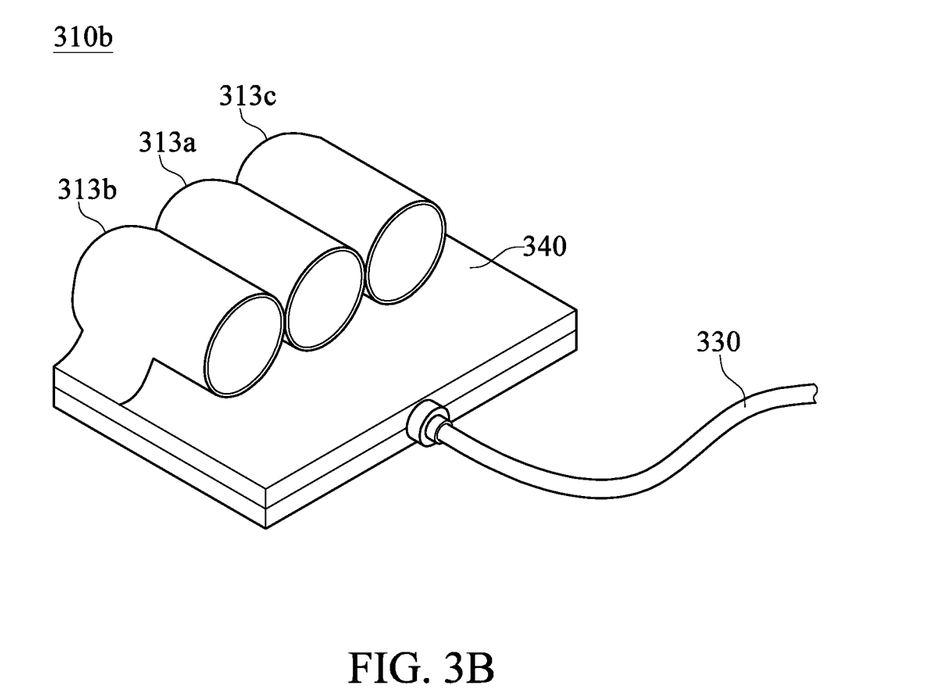
FIG. 3B is a schematic view showing an appearance of a capacitive accelerometer device depicted in accordance with another exemplary embodiment of the present disclosure.
Figure 3C:
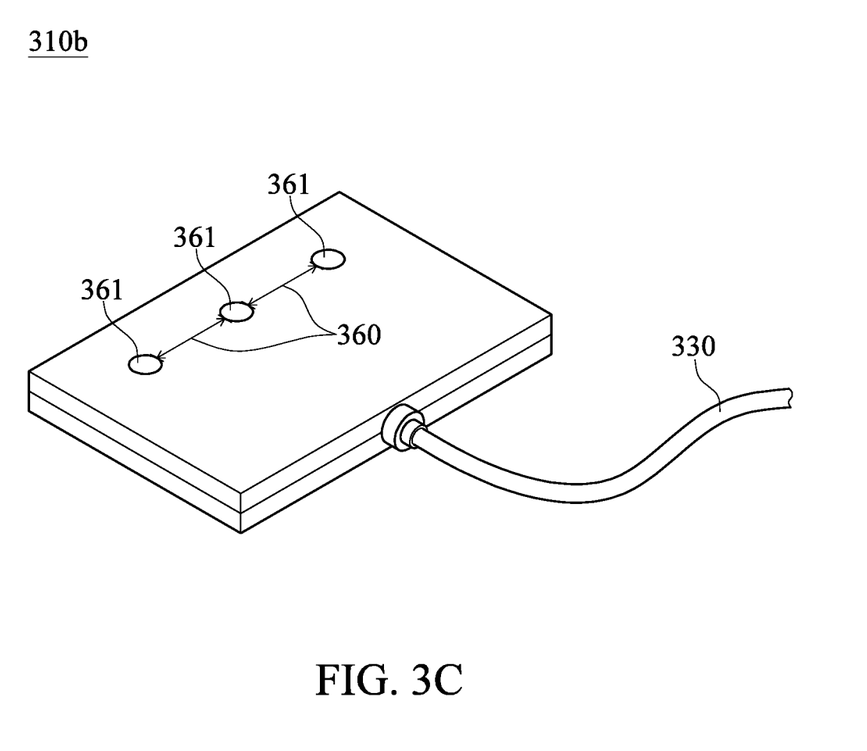
FIG. 3C is a schematic view showing an appearance of rear side of a capacitive accelerometer device depicted in accordance with another exemplary embodiment of the present disclosure.

Reference is next made to FIGS. 3B and 3C. FIG. 3B s is a schematic view showing an appearance of a capacitive accelerometer device depicted in accordance with another exemplary embodiment of the present disclosure. FIG. 3C is a schematic view showing an appearance of rear side of a capacitive accelerometer device depicted in accordance with another exemplary embodiment of the present disclosure.

The capacitive accelerometer module 310b has a finger sleeving 313a, a finger sleeving 313b, a finger sleeving 313c, a signal line 330 and a circuit board 340. The finger sleeving 313a, the finger sleeving 313b and the finger sleeving 313c are used for being sleeved on an index finger, a middle finger and a ring finger of the user. The capacitive accelerometers 361 are disposed on a side of the finger sleeving 313a, the finger sleeving 313b and the finger sleeving 313c and are separated by one finger gap from each other. For example, the capacitive accelerometers can be disposed on the other side of a contact point between the finger sleeving 313a, the finger sleeving 313b, the finger sleeving 313c and the circuit board 340 (a back side of the circuit board 340). The capacitive accelerometers sense the arterial acceleration pulse wave of the user through a pulse received by the finger sleeving 313a, the finger sleeving 313b and the finger sleeving 313c.

Figure 3D:
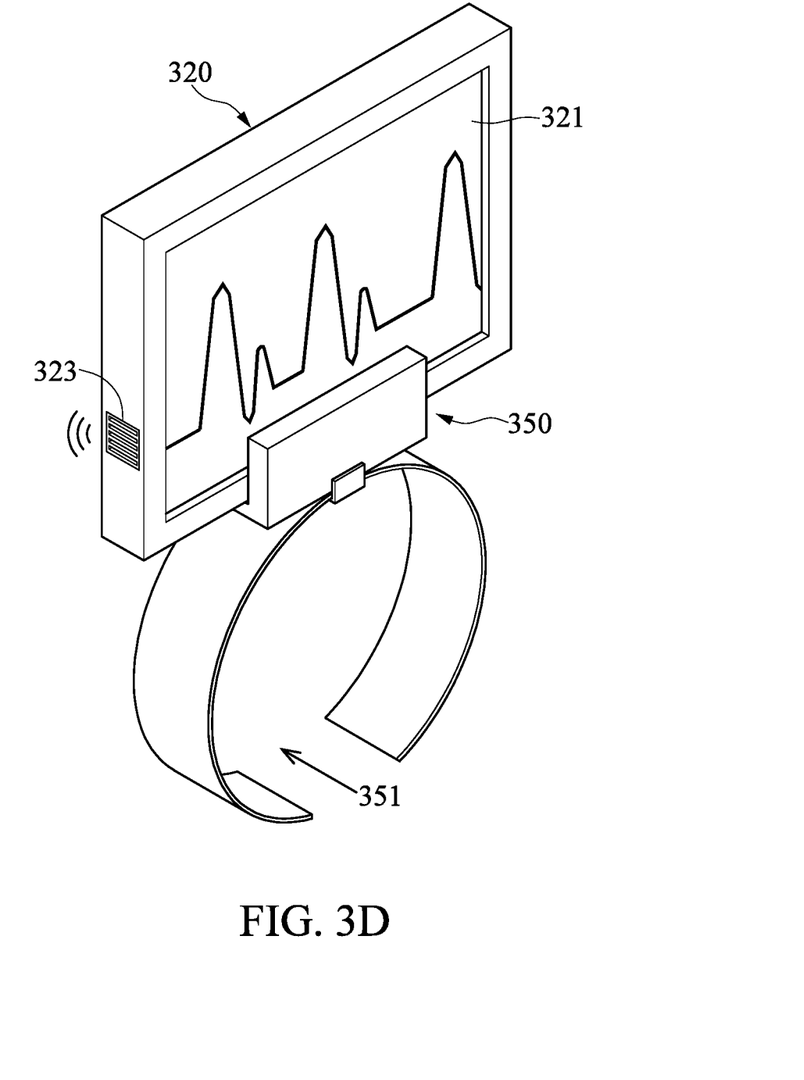
FIG. 3D is a schematic view showing an appearance of a display device depicted in accordance with an exemplary embodiment of the present disclosure.

Reference is next made to FIG. 3D, which is a schematic view showing an appearance of a display device depicted in accordance with an exemplary embodiment of the present disclosure.

The display device 320 includes a displayer 321 and a speaker 323. The displayer 321 is used to display the arterial acceleration pulse wave of the user. The speaker 323 emits an audible signal according to a change value of the arterial acceleration pulse wave. For example, the audible signal may be a 3-second short tone. The display device 320 connects to a fixing bracket 350 via a connector (not shown). The fixing bracket 350 has a clasp 351 for snapping the display device 320 on a wrist of the user.

Figure 4A:
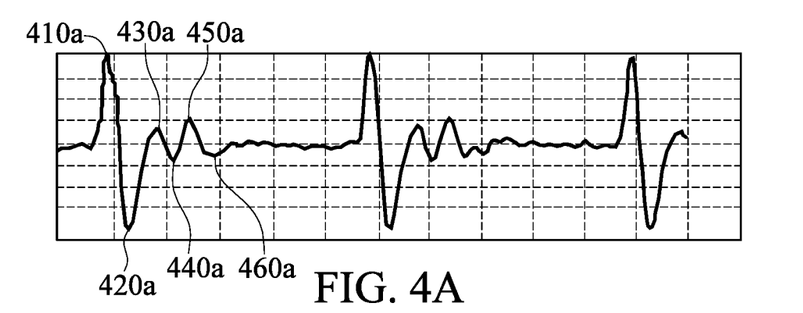
FIG. 4A is an oscilloscope diagram taken before meal as shown on a displayer in accordance with an exemplary embodiment of the present disclosure.
Figure 4B:
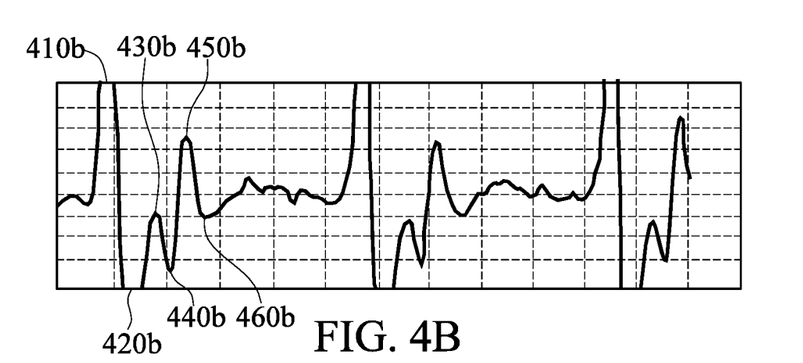
FIG. 4B is an oscilloscope diagram taken 1 hour after meal as shown on a displayer in accordance with an exemplary embodiment of the present disclosure.
Figure 4C:
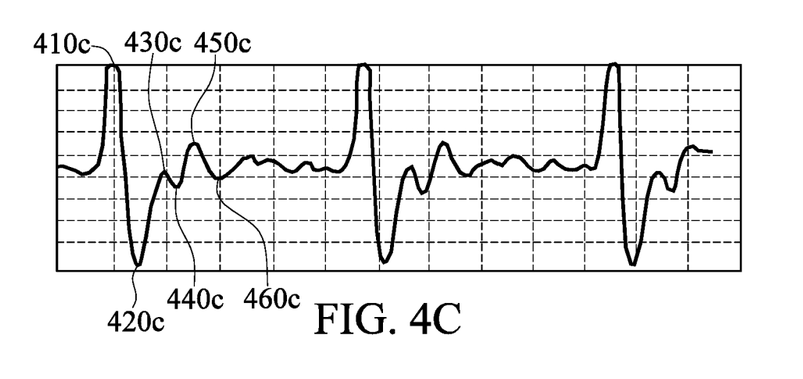
FIG. 4C is an oscilloscope diagram taken 2 hours after meal as shown on a displayer in accordance with an exemplary embodiment of the present disclosure.
Figure 4D:
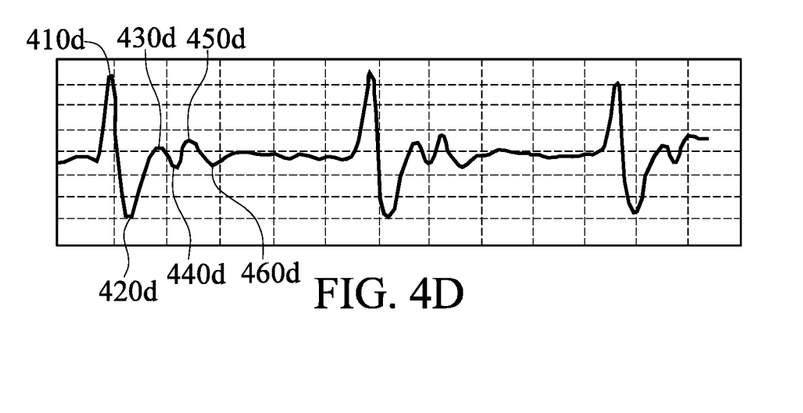
FIG. 4D is an oscilloscope diagram taken 3 hours after meal as shown on a displayer in accordance with an exemplary embodiment of the present disclosure.

Reference is made to FIGS. 4A, 4B, 4C and 4D. FIG. 4A is an oscilloscope diagram taken before meal as shown on a displayer in accordance with an exemplary embodiment of the present disclosure. FIG. 4B is an oscilloscope diagram taken 1 hour after meal as shown on a displayer in accordance with an exemplary embodiment of the present disclosure. FIG. 4C is an oscilloscope diagram taken 2 hours after meal as shown on a displayer in accordance with an exemplary embodiment of the present disclosure. FIG. 4D is an oscilloscope diagram taken 3 hours after meal as shown on a displayer in accordance with an exemplary embodiment of the present disclosure.

The oscilloscope diagram of FIG. 4A includes a Q wave 410a, a R wave 420a, a S wave 430a, a T wave 440a, an U wave 450a and a V wave 460a.

The oscilloscope diagram of FIG. 4B includes a Q wave 410b, a R wave 420b, a S wave 430b, a T wave 440b, an U wave 450b and a V wave 460b.

The oscilloscope diagram of FIG. 4C includes a Q wave 410c, a R wave 420c, a S wave 430c, a T wave 440c, an U wave 450c and a V wave 460c.

The oscilloscope diagram of FIG. 4D includes a Q wave 410d, a R wave 420d, a S wave 430d, a T wave 440d, an U wave 450d and a V wave 460d.

In a comparison between the oscilloscope diagrams before a meal and 1 hour after meal, the R wave 420b, the S wave 430b and the T wave 440b are significantly lower than the R wave 420a, the S wave 430a and the T wave 440a. The U wave 450b is significantly higher than the U wave 450a.

In a comparison between the oscilloscope diagrams 1 hour after meal and 2 hours after meal, the R wave 420c, the S wave 430c and the T wave 440c are significantly higher than the R wave 420b, the S wave 430b and the T wave 440b. The U wave 450c is significantly lower than the U wave 450b.

In a comparison between the oscilloscope diagrams 3 hours after meal and before a meal, the Q wave 410d, the R wave 420d, the S wave 430d, the T wave 440d, the U wave 450d and the V wave 460d are similar to the Q wave 410a, the R wave 420a, the S wave 430a, the T wave 440a, the U wave 450a and the V wave 460a. This comparison result represents that the arterial acceleration pulse wave of the user has approached a steady state at 3 hours after meal.

In an embodiment of the present disclosure, the condenser microphone is used to collect sound waveforms transmitted in the air, including the main sound and all ambient noise. The condenser microphone is adhered on the skin to sense the arterial acceleration pulse wave. Based on a distance variation principle of capacitor electrodes in a capacitive accelerometer, when the active diaphragm is changed by an external force shockwave to change a gap (d) between fixed electrodes, a capacitance value C is changed, where the capacitance value $C=\varepsilon*S/d$, $\varepsilon$=dielectric constant, S=electrode plate area, d=two electrode plate gap. The capacitance value changes according to the acceleration value. The condenser microphone and the capacitive accelerometer have the same operating principle and become a vibrating capacitive accelerometer, so as to convert and obtain an acceleration pulse wave that is resistant to environmental sound interference. In addition, the condenser microphone can also be used in a smart phone, a smart bracelet, an ear-hook detection device, a headset smart glasses, etc. When the capacitive accelerometer is applied to a smart phone, the smart phone can have a jack. For example, the jack may be a headphone jack, a USB jack, a micro USB jack, a type-C jack or a charging jack. The capacitive accelerometer module is connected to the jack of the mobile device, and each of the capacitive accelerometers is used to sense and recognize the arterial acceleration pulse wave of the user in a contact manner via a built-in program in the mobile device. In addition, the capacitive accelerometer module can be built-in in the mobile device or externally connected to the jack of the mobile device.

In an embodiment of the present disclosure, the condenser microphone is used to sense an arterial velocity pulse wave and convert it into an acceleration pulse wave. The acceleration pulse wave includes a baseline and six waves. Deviation of six waves from baseline reflects vascular physiological status. Blood glucose rising after a meal increases a blood viscosity and a blood viscosity coefficient. According to Poiseuille's law, a blood flow resistance R is equal to $(8\eta\Delta\chi)/(\pi r^4)$, where $\eta$=blood viscosity coefficient, $\Delta\chi$=vascular unit length, $\pi$=pi, r=vascular radius. The blood flow resistance in the vascular is proportional to the blood viscosity coefficient, which causes the blood flow velocity to decrease. The six waves of the arterial acceleration pulse wave vary with blood glucose fluctuations.

Reference is made to FIGS. 4A-4D, first, a pulse wave before a meal with an empty stomach is measured as the user's basic acceleration pulse wave or the user's basic blood glucose level. Next, a pulse wave 1 hour after meal is measured as an acceleration pulse wave or a blood glucose 1 hour after meal. Next, pulse waves 2 hours after meal and 3 hours after meal are measured to individually obtain acceleration pulse waves 2 hours after meal and 3 hours after meal. The deviation and recovery of the six waves and the baselines of the acceleration pulse waves before a meal, 1 hour after meal, after 2 hours meal and 3 hours after meal are compared. Usually, the waves of the acceleration pulse wave 3 hours after meal will return to the waves of the acceleration pulse wave before a meal as the blood glucose fluctuation of a person.

In an embodiment of the present disclosure, the capacitive accelerometer device can be used to sense a blood pressure of the user to analyze the difference by waves of a systolic phase and a diastolic phase waveform deviating from the baseline. When the blood pressure rises, the heart rate will rise by more than 20%, and the R wave will shift upward and the S wave will shift downward.

In an embodiment of the present disclosure, the capacitive accelerometer device can be used to sense a vascular age of the user. The Q wave represents a starting point at a beginning of a ventricular systolic phase. The R wave represents a peak value of the systolic phase. The S wave represents a cut point of a reflected wave, which may also be referred to as a reflection point of a fine artery. The T wave represents a peak value of the reflected wave at the end of the systolic phase. The U wave represents an arterial notch as the end of the ventricular systolic phase. The V wave represents a peak value of the diastolic phase, and a raised wave at a beginning of a ventricular diastolic phase is a reflected wave of aortic valve closure. The interval from the Q wave to the next Q wave is a pulse heart rate. A period from the Q wave to U wave represents the ventricular systolic phase. A period from the U wave and the next Q wave rising at a starting point of the baseline represents the ventricular diastolic phase.

Figure 5:
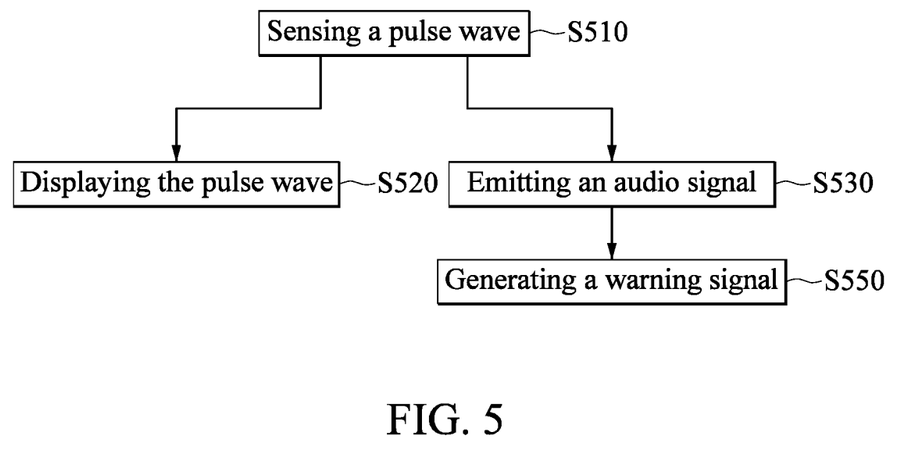
FIG. 5 shows a flow chart of a sensing method in accordance with an exemplary embodiment of the present disclosure.

Reference is made to FIGS. 1 and 5. FIG. 5 shows a flow chart of a sensing method in accordance with an exemplary embodiment of the present disclosure. The sensing method is applied to the capacitive accelerometer device 100 and used to sense the arterial acceleration pulse wave of the user.

In step S510, one or more capacitive accelerometers 111 of the capacitive accelerometer module 110 sense the arterial acceleration pulse wave of the user in a contact manner.

In step S520, the displayer 121 of the display device 120 displays the arterial acceleration pulse wave of the user.

In step S530, the speaker 123 of the display device 120 emits the audible signal according to the change value of the arterial acceleration pulse wave. The display device 120 connects to the fixing bracket via the connector, and the fixing bracket has a clasp for snapping the display device 120 on the wrist of the user.

In step S550, the display device 120 automatically senses the arterial acceleration pulse wave of the user and correspondingly generates the change value. The display device 120 generates a prompt signal when the change value is equal to or larger than a predetermined value.

In an embodiment, the display device 120 is used to sense the arterial acceleration pulse waves of the user before and after a meal. The display device 120 generates a heart rate signal, blood viscosity signal and vascular age signal according to the arterial acceleration pulse waves of the user before and after a meal.

Figure 6A:
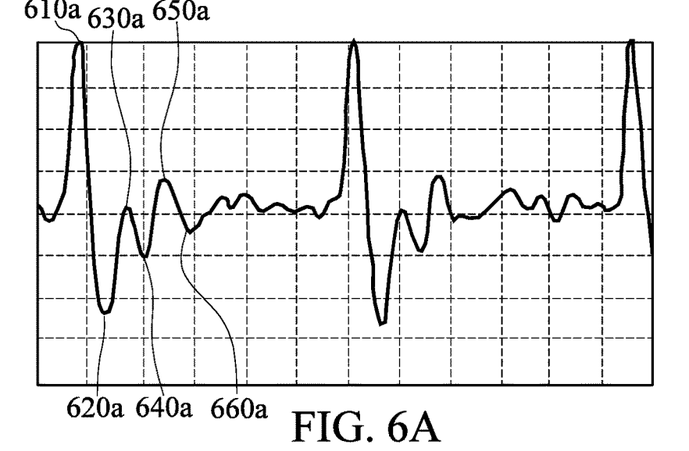
FIG. 6A is an oscilloscope diagram taken before jogging as shown on a displayer in accordance with an exemplary embodiment of the present disclosure.
Figure 6B:
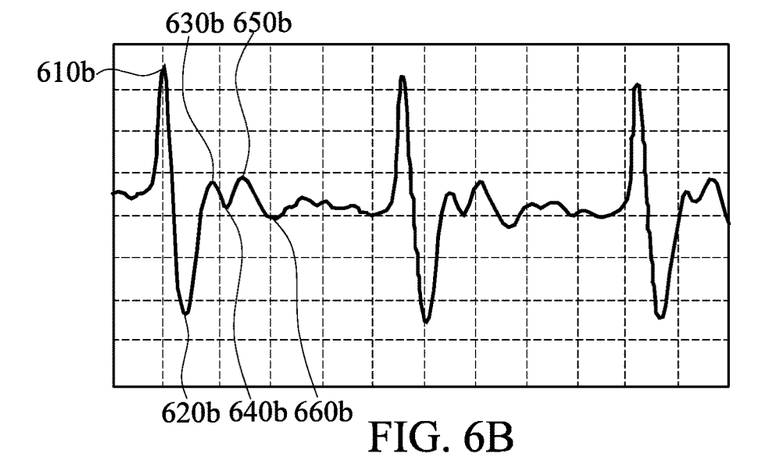
FIG. 6B is an oscilloscope diagram taken 4 hours after jogging as shown on a displayer in accordance with an exemplary embodiment of the present disclosure.
Figure 6C:
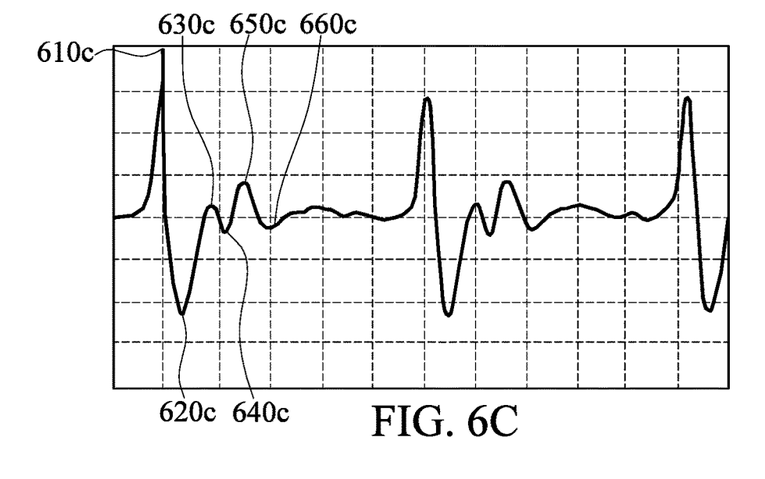
FIG. 6C is an oscilloscope diagram taken 7 hours after jogging as shown on a displayer in accordance with an exemplary embodiment of the present disclosure.

Reference is made to FIGS. 6A, 6B and 6C. FIG. 6A is an oscilloscope diagram taken before jogging as shown on a displayer in accordance with an exemplary embodiment of the present disclosure. FIG. 6B is an oscilloscope diagram taken 4 hours after jogging as shown on a displayer in accordance with an exemplary embodiment of the present disclosure. FIG. 6C is an oscilloscope diagram taken 7 hours after jogging as shown on a displayer in accordance with an exemplary embodiment of the present disclosure.

The oscilloscope diagram of FIG. 6A includes a Q wave 610*a*, a R wave 620*a*, a S wave 630*a*, a T wave 640*a*, an U wave 650*a* and a V wave 660*a*.

The oscilloscope diagram of FIG. 6B includes a Q wave 610*b*, a R wave 620*b*, a S wave 630*b*, a T wave 640*b*, an U wave 650*b* and a V wave 660*b*.

The oscilloscope diagram of FIG. 6C includes a Q wave 610*c*, a R wave 620*c*, a S wave 630*c*, a T wave 640*c*, an U wave 650*c* and a V wave 660*c*.

Exercise redistributes the blood of limbs and organs of the human body, shrinks and expands the micro arteries and microvessels of muscle tissue and organs, thereby promoting a microcirculation to provide nutrients and promote metabolism. In a comparison between the oscilloscope diagrams before jogging and 4 hours after jogging, the S wave rising above the baseline represents promoting a vascular elasticity and delaying a reflected wave of the systolic phase. The T wave rises to the baseline. Amplitudes of the S wave and the T wave decreasing represent decreasing residual blood of the radial artery and increasing a blood perfusion of the micro arteries. Accordingly, the microcirculation is improved.

The capacitive accelerometer device of the present disclosure can sense the arterial acceleration pulse wave of the user before and after a medication, the exercise, etc., to illustrate changes of the arterial acceleration pulse wave of the user, where the changes of the arterial acceleration pulse wave of the user represent a change of the microcirculation of the user.

In summary, the condenser microphone used in the capacitive accelerometer device of the present disclosure can increase the accuracy of sensing the arterial acceleration pulse wave of the user and decrease the manufacturing costs. The capacitive accelerometer is connected to the capacitive accelerometer module by snap-fastening to increase the flexibility in replacing the capacitive accelerometer and the cleanliness in use. The display device sends the prompt signal when the arterial acceleration pulse wave automatically senses that a preset value is exceeded in a time range, so as to implement the function of remote medical detection.

The descriptions illustrated supra set forth simply the preferred embodiments of the instant disclosure; however, the characteristics of the instant disclosure are by no means restricted thereto. All changes, alterations, or modifications conveniently considered by those skilled in the art are deemed to be encompassed within the scope of the instant disclosure delineated by the following claims.

What is claimed is:

1. A capacitive accelerometer device, adapted to sense an arterial acceleration pulse wave of a user, comprising:
   a capacitive accelerometer module, including a plurality of vibrating capacitive accelerometer, wherein the plurality of vibrating capacitive accelerometers includes an active diaphragm that establishes direct contact with a skin of the user for directly sensing the arterial acceleration pulse wave of the user, and each period of the arterial acceleration pulse wave includes six waves, and the six waves include a Q wave, an R wave, an S wave, a T wave, a U wave and a V wave, wherein when each of the plurality of vibrating capacitive accelerometer is adhered to the skin of the user, the active diaphragm is changed directly by the skin of the user, such that a capacitance value is changed according to an acceleration value, thereby obtaining an acceleration pulse wave that is resistant to environmental sound interference; and
   a display device, electrically connected to the capacitive accelerometer module and including a displayer and a speaker, the displayer displaying the arterial acceleration pulse wave of the user, the speaker emitting an audible signal according to change values of the Q wave, the R wave, the S wave, the T wave, the U wave and the V wave of the arterial acceleration pulse wave, the display device connecting to a fixing bracket via a connector, the fixing bracket having a clasp for snapping the display device on a wrist of the user;
   wherein the display device further includes a central processor, and the central processor automatically receives the arterial acceleration pulse wave of the user, generates values of the Q wave, the R wave, the S wave, the T wave, the U wave and the V wave of the arterial acceleration pulse wave at different timings, and correspondingly generates the change values of the Q wave, the R wave, the S wave, the T wave, the U wave and the V wave of the arterial acceleration pulse wave according to the values of the Q wave, the R wave, the S wave, the T wave, the U wave and the V wave at the different timings, the display device generates a prompt signal when one of the change values of the Q wave, the R wave, the S wave, the T wave, the U wave and the V wave is equal to or larger than a predetermined value at a predetermined time interval, the Q wave represents a starting point at a beginning of a ventricular systolic phase, the R wave represents a peak value of the ventricular systolic phase, the S wave represents a cut point of a reflected wave, the T wave represents a peak value of the reflected wave at an end of the ventricular systolic phase, the U wave represents an arterial notch as the end of the ventricular systolic phase, and the V wave represents a peak value of a diastolic phase, wherein the capacitive accelerometer module includes finger sleevings used for being sleeved on an index finger, a middle finger and a ring finger of the user, each of the plurality of vibrating capacitive accelerometers is disposed on a side of each of the finger sleevings, the plurality of vibrating capacitive accelerometers are disposed on the same side of the finger sleevings and thus separated by a same sized gap from each other, and the plurality of vibrating capacitive accelerometers sense the arterial acceleration pulse wave of the user through a pulse received by the finger sleevings.

2. The capacitive accelerometer device according to claim 1, wherein each of the plurality of the vibrating capacitive accelerometers is a condenser microphone.

3. The capacitive accelerometer device according to claim 2, wherein the condenser microphone is an electret condenser microphone or a micro-electromechanical condenser microphone.

4. The capacitive accelerometer device according to claim 1, wherein each of the plurality of vibrating capacitive accelerometers connects to the capacitive accelerometer module by snap-fastening.

5. The capacitive accelerometer device according to claim 1, wherein the display device receives the arterial acceleration pulse wave of the user before and after a meal, the display device generates, according to the six waves generated from the arterial acceleration pulse wave of the user before and after the meal, a blood viscosity signal and a vascular age signal.

6. The capacitive accelerometer device according to claim 1, wherein the changes of the arterial acceleration pulse wave of the user represent a change of a microcirculation of the user.

7. A sensing method, performed with a capacitive accelerometer device, applied to sense an arterial acceleration pulse wave of a user, the method comprising:

sensing the arterial acceleration pulse wave of the user directly by a plurality of vibrating capacitive accelerometer included in a capacitive accelerometer module, wherein the vibrating capacitive accelerometer includes an active diaphragm that establishes direct contact with a skin of the user for directly sensing the arterial acceleration pulse wave of the user, and each period of the arterial acceleration pulse wave includes six waves, the six waves include a Q wave, an R wave, an S wave, a T wave, a U wave and a V wave, and the plurality of vibrating capacitive accelerometers directly contact with a skin of the user, wherein when each of the plurality of vibrating capacitive accelerometers is adhered to the skin of the user, the active diaphragm is changed directly by the skin of the user, such that a capacitance value is changed according to an acceleration value, thereby obtaining an acceleration pulse wave that is resistant to environmental sound interference;

displaying the arterial acceleration pulse wave of the user by a displayer of a display device; and emitting an audible signal according to change values of the Q wave, the R wave, the S wave, the T wave, the U wave and the V wave of the arterial acceleration pulse wave by a speaker included in a display device, wherein the display device connects to a fixing bracket via a connector, the fixing bracket having a clasp for snapping the display device on a wrist of the user;

wherein a central processor of the display device automatically receives the arterial acceleration pulse wave of the user, generates values of the Q wave, the R wave, the S wave, the T wave, the U wave and the V wave of the arterial acceleration pulse wave at different timings, and correspondingly generates the change values of the Q wave, the R wave, the S wave, the T wave, the U wave and the V wave of the arterial acceleration pulse wave according to the values of the Q wave, the R wave, the S wave, the T wave, the U wave and the V wave at the different timings, the display device generates a prompt signal when one of the change values of the Q wave, the R wave, the S wave, the T wave, the U wave and the V wave of the arterial acceleration pulse wave is equal to or larger than a predetermined value at a predetermined time interval, the Q wave represents a starting point at a beginning of a ventricular systolic phase, the R wave represents a peak value of the ventricular systolic phase, the S wave represents a cut point of a reflected wave, the T wave represents a peak value of the reflected wave at an end of the ventricular systolic phase, the U wave represents an arterial notch as the end of the ventricular systolic phase, and the V wave represents a peak value of a diastolic phase, wherein the capacitive accelerometer module includes finger sleevings used for being sleeved on an index finger, a middle finger and a ring finger of the user, each of the plurality of vibrating capacitive accelerometers is disposed on a side of each of the finger sleevings, the plurality of vibrating capacitive accelerometers are disposed on the same side of the finger sleevings and thus separated by a same sized gap from each other, and the plurality of vibrating capacitive accelerometers sense the arterial acceleration pulse wave of the user through a pulse received by the finger sleevings.

8. The sensing method according to claim 7, wherein the display device receives the arterial acceleration pulse wave of the user before and after a meal, the display device generates, according to the six waves generated from the arterial acceleration pulse wave of the user before and after the meal, a blood viscosity signal and a vascular age signal.

9. The sensing method according to claim 7, wherein the changes of the arterial acceleration pulse wave of the user represent a change of a microcirculation of the user.

* * * * *